US006184266B1

(12) United States Patent
Ronan et al.

(10) Patent No.: US 6,184,266 B1
(45) Date of Patent: Feb. 6, 2001

(54) MEDICAL DEVICES COMPRISING CROSS-LINKED HYDROGELS HAVING IMPROVED MECHANICAL PROPERTIES

(75) Inventors: John M. Ronan; Samuel A. Thompson, both of New Castle, DE (US)

(73) Assignee: Scimed Life Systems, Inc., Maple Grove, MN (US)

( * ) Notice: Under 35 U.S.C. 154(b), the term of this patent shall be extended for 0 days.

(21) Appl. No.: 09/496,709

(22) Filed: Feb. 2, 2000

Related U.S. Application Data

(63) Continuation of application No. 08/679,609, filed on Jul. 11, 1996, now Pat. No. 6,060,534.

(51) Int. Cl.$^7$ .................. A61K 9/22; C08K 3/24
(52) U.S. Cl. ............... 523/113; 523/135; 524/28; 524/503; 524/916; 525/903; 536/3; 424/78.17; 424/422; 604/264; 623/1
(58) Field of Search ................... 523/105, 113; 524/28, 503, 916; 525/903; 536/3; 424/78.17, 422; 604/264; 623/1

(56) References Cited

U.S. PATENT DOCUMENTS

| | | |
|---|---|---|
| 4,279,251 | 7/1981 | Rüsch ................... 128/348 |
| 4,286,341 | 9/1981 | Greer et al. ................. 3/1.4 |
| 4,582,865 | 4/1986 | Balazs et al. ............. 524/29 |
| 4,605,691 | 8/1986 | Balazs et al. ............. 524/27 |
| 4,613,517 | 9/1986 | Williams et al. ............ 427/2 |
| 4,636,524 | 1/1987 | Balazs et al. ............ 514/781 |
| 4,638,059 | 1/1987 | Sutherland ............. 536/121 |
| 4,674,506 | 6/1987 | Alcond ................. 128/334 |
| 4,700,704 | 10/1987 | Jamiolkowski et al. ...... 128/335.5 |
| 4,705,039 | 11/1987 | Sakaguchi et al. ........ 128/334 |
| 4,716,154 | 12/1987 | Mälson et al. ............. 514/54 |
| 4,716,224 | 12/1987 | Sakurai et al. .......... 536/55.1 |
| 4,791,929 | 12/1988 | Jarrett et al. ............ 128/335.5 |
| 4,801,475 | 1/1989 | Halpern et al. ............ 427/338 |
| 4,826,945 | 5/1989 | Cohn et al. ............... 528/76 |
| 4,863,472 | 9/1989 | Törmälä et al. ........... 623/16 |
| 4,863,907 | 9/1989 | Sakurai et al. ............ 514/56 |
| 4,871,365 | 10/1989 | Dumican ................. 623/11 |
| 4,874,360 | 10/1989 | Goldberg et al. ............ 604/8 |
| 4,878,907 | 11/1989 | Okada et al. ............. 623/1 |
| 4,886,870 | 12/1989 | D'Amore et al. .......... 528/206 |
| 4,888,016 | 12/1989 | Langerman ............... 623/6 |
| 4,902,295 | 2/1990 | Walthall et al. ............ 623/11 |
| 4,906,237 | 3/1990 | Johansson et al. .......... 604/265 |
| 4,916,193 | 4/1990 | Tang et al. .............. 525/413 |
| 4,941,870 | 7/1990 | Okada et al. ............. 600/36 |
| 4,948,575 | 8/1990 | Cole et al. ............... 424/44 |
| 4,950,258 | 8/1990 | Kawai et al. ............. 604/281 |
| 4,957,744 | 9/1990 | Della Valle et al. ........ 424/401 |
| 4,958,038 | 9/1990 | Smeltz .................. 556/55 |
| 4,965,353 | 10/1990 | Della Valle et al. ........ 536/55.1 |
| 4,994,074 | 2/1991 | Bezwada et al. .......... 606/230 |
| 4,997,443 | 3/1991 | Walthall et al. ........... 623/11 |
| 5,049,138 | 9/1991 | Chevalier et al. .......... 604/265 |
| 5,057,606 | 10/1991 | Garbe .................. 536/54 |
| 5,061,738 | 10/1991 | Solomon et al. .......... 523/100 |
| 5,064,057 | 11/1991 | Iwatsuki et al. .......... 606/154 |
| 5,077,033 | 12/1991 | Viegas et al. ........... 424/78.04 |
| 5,085,629 | 2/1992 | Goldberg et al. ............ 604/8 |
| 5,089,606 | 2/1992 | Cole et al. ............... 536/54 |
| 5,128,326 | 7/1992 | Balazs et al. ............ 514/54 |
| 5,141,516 | 8/1992 | Detweiler .............. 606/154 |
| 5,144,016 | 9/1992 | Skjak-Braek et al. ......... 536/3 |
| 5,147,399 | 9/1992 | Dellon et al. ............ 623/12 |
| 5,160,341 | 11/1992 | Brenneman et al. ........ 606/198 |
| 5,200,195 | 4/1993 | Dong et al. ............. 424/464 |
| 5,292,525 | 3/1994 | Brenden et al. ........... 424/601 |
| 5,306,286 | 4/1994 | Stack et al. ............. 606/198 |
| 5,308,701 | 5/1994 | Cohen et al. ........... 428/402.22 |
| 5,322,935 | 6/1994 | Smith ................... 536/20 |
| 5,324,519 | 6/1994 | Dunn et al. ............. 424/426 |
| 5,334,640 | 8/1994 | Desai et al. ............. 524/56 |
| 5,401,257 | 3/1995 | Chevalier et al. ......... 604/265 |
| 5,425,739 | 6/1995 | Jessen ................. 606/155 |
| 5,425,949 | 6/1995 | Bennett et al. ........... 424/426 |
| 5,428,123 | 6/1995 | Ward et al. .............. 528/25 |
| 5,443,458 | 8/1995 | Eury .................. 604/891.1 |
| 5,444,113 | 8/1995 | Sinclair et al. ........... 524/306 |
| 5,489,297 | 2/1996 | Duran ................... 623/2 |
| 5,502,158 | 3/1996 | Sinclair et al. ........... 528/354 |
| 5,527,324 | 6/1996 | Krantz et al. ............ 606/155 |
| 5,527,337 | 6/1996 | Stack et al. ............. 606/198 |
| 5,531,716 | 7/1996 | Luzio et al. ............. 604/265 |
| 5,531,735 | 7/1996 | Thompson .............. 604/891.1 |
| 5,541,234 | 7/1996 | Unger et al. ............. 521/66 |

(List continued on next page.)

FOREIGN PATENT DOCUMENTS

| | | |
|---|---|---|
| 0 341 745 A1 | 11/1989 | (EP) . |
| 0507604A2 | 4/1992 | (EP) . |
| 0507604A3 | 4/1992 | (EP) . |
| 0645150A1 | 9/1994 | (EP) . |
| 2 151 244 | 7/1985 | (GB) . |
| 870271692 | 10/1987 | (JP) . |
| 4-146218 | 5/1992 | (JP) . |
| 9218098 | 10/1992 | (WO) . |
| 9309176 | 5/1993 | (WO) . |

*Primary Examiner*—Peter A. Szekely
(74) *Attorney, Agent, or Firm*—Testa, Hurwitz & Thibeault, LLP

(57) ABSTRACT

Shaped medical devices, e.g. stents, having improved mechanical properties and structural integrity are disclosed. The devices comprise shaped polymeric hydrogels which are both ionically and non-ionically crosslinked and which exhibit improved structural integrity after selective removal of the crosslinking ions. Process for making such devices are also disclosed wherein an ionically crosslinkable polymer is both ionically and non-ionically crosslinked to form a shaped medical device. When implanted in the body, selective in-vivo stripping of the crosslinking ions produces a softer, more flexible implant having improved structural integrity.

30 Claims, No Drawings

U.S. PATENT DOCUMENTS

| | | | |
|---|---|---|---|
| 5,541,304 | 7/1996 | Thompson | 536/20 |
| 5,543,218 | 8/1996 | Bennett et al. | 428/375 |
| 5,578,662 | 11/1996 | Bennett et al. | 524/54 |
| 5,629,077 | 5/1997 | Turnlund et al. | 442/38 |
| 5,670,161 | 9/1997 | Healy et al. | 424/426 |
| 5,674,241 | 10/1997 | Bley et al. | 606/198 |
| 5,674,287 | 10/1997 | Slepian et al. | 623/11 |
| 5,690,961 | 11/1997 | Nguyen | 424/488 |
| 5,709,877 | 1/1998 | Della Valle et al. | 424/444 |
| 5,713,852 | 2/1998 | Anthony et al. | 604/49 |
| 5,718,916 | 2/1998 | Scherr | 424/445 |
| 5,736,595 | 4/1998 | Günther et al. | 524/28 |
| 5,830,217 | 10/1998 | Ryan | 606/108 |

MEDICAL DEVICES COMPRISING CROSS-LINKED HYDROGELS HAVING IMPROVED MECHANICAL PROPERTIES

CROSS-REFERENCE TO RELATED APPLICATIONS

This application claims priority under 35 U.S.C. §120 as a continuation application of U.S. patent application Ser. No. 08/679,609, filed Jul. 11, 1996, now U.S. Pat. No. 6,060,534. The entirety of this application is hereby incorporated herein by reference.

BACKGROUND OF THE INVENTION

1. Field of the Invention

This invention relates to medical devices comprising polymer hydrogels having improved mechanical properties.

2. Description of Related Art

Medical devices adapted for implant into the body to facilitate the flow of bodily fluids, to serve as vascular grafts or for other purposes have been developed. Typically, these devices include stents, catheters or cannulas, plugs, constrictors, tissue or biological encapsulants and the like.

Typically, many of these devices used as implants are made of durable, non-degradable plastic materials such as polyurethanes, polyacrylates, silicone polymers and the like, or more preferably from biodegradable polymers which remain stable in-vivo for a period of time but eventually biodegrade in-vivo into small molecules which are removed by the body by normal elimination in the urine or feces.

Typical of such biodegradable polymers are polyesters, polyanhydrides and polyorthoesters which undergo hydrolytic chain cleavage, as disclosed in U.S. Pat. No. 5,085,629; crosslinked polysaccharide hydrogel polymers as disclosed in EPA 0507604 A-2 and U.S. Pat. No. 5,057,606 and other ionically crosslinked hydrogels as disclosed in U.S. Pat. Nos. 4,941,870, 4,286,341 and 4,878,907.

EPA 0645150 A-1 describes hydrogel medical devices prepared from ionically crosslinked anionic polymers, e.g. polysaccharides such as calcium alginate or ionically crosslinked cationic polymers such as chitosan, cationic guar, cationic starch and polyethylene amine. These devices are adapted for more rapid in-vivo disintegration upon the administration of a chemical trigger material which displaces crosslinking ions.

Hydrogels offer excellent biocompatibility and have been shown to have reduced tendency for inducing thrombosis, encrustation, and inflammation. Unfortunately, the use of hydrogels in biomedical device applications has often been hindered by poor mechanical performance. Although many medical device applications exist where minimal stresses are encountered by the device in-vivo, most applications require that the device survive high stresses during implantation. Hydrogels suffer from low modulus, low yield stress and low strength when compared to non-swollen polymer systems. Lower mechanical properties result from the swollen nature of hydrogels and the non-stress bearing nature of the swelling agent, e.g., aqueous fluids.

Accordingly, there is a need in the art to provide shaped medical devices which not only offer the advantages of polymer hydrogels in terms of biological compatibility, but which also have improved mechanical properties, e.g. improved strength and modulus properties, such that they retain their shape and stiffness during insertion into the body, such as by delivery through an endoscope, and which also can swell and soften inside the body to enhance patient comfort.

SUMMARY OF THE INVENTION

This invention provides a means of boosting the mechanical performance of shaped medical devices comprising polymer hydrogels, such as stents, so that they may be more easily inserted into the body, and at the same time provides a means to soften such devices in-vivo while retaining the structural integrity of the device.

The invention provides a process for improving the mechanical properties and structural integrity of a shaped medical device comprising a crosslinked polymeric hydrogel, said process comprising subjecting an ionically crosslinkable polymer composition to crosslinking conditions such that both ionic and non-ionic crosslinks are formed resulting in a polymeric hydrogel, wherein a medical device of improved structural integrity is obtained upon selective removal of said crosslinking ions from said polymeric hydrogel.

In addition, the invention also provides a process for improving the mechanical properties and structural integrity of a shaped medical device comprising a polymeric hydrogel, said process comprising:

a) providing a crosslinked polymeric hydrogel composition containing a non-ionic crosslink structure, said hydrogel polymer characterized as being ionically crosslinkable and having a primary shape;

b) imparting a secondary shape to said hydrogel polymer composition; and c) subjecting said hydrogel polymer to ionic crosslinking conditions to ionically crosslink said hydrogel polymer while retaining said secondary shape.

A medical device substantially conforming to the primary shape of said hydrogel is obtained upon selective removal of the crosslinking ions from said crosslinked polymeric hydrogel, such as by removal of said ions after the device is implanted into the body.

The invention also provides a shaped medical device having improved mechanical properties comprising a crosslinked polymeric hyciogel, said hydrogel containing both an ionic and a non-ionic crosslink structure. The device is characterized by improved structural integrity after selective removal of said ionic crosslinking ions as compared with an otherwise identical device containing only an ionic structure.

The invention further provides a medical procedure comprising insertion of the above-described medical device into a human or animal body to form an implant, followed by the selective removal of at least a portion of the crosslinking ions from the implant in-vivo to soften the implant. Where the implant is later surgically removed, it may be once again subjected to ionic crosslinking conditions to ionically re-crosslink the implant prior to removal from the body.

DETAILED DESCRIPTION OF THE INVENTION

The ionically crosslinkable polymers from which the medical devices of this invention may be fabricated may be anionic or cationic in nature and include but are not limited to carboxylic, sulfate, hydroxy and amine functionalized polymers, normally referred to as hydrogels after being crosslinked. The term "hydrogel" indicates a crosslinked, water insoluble, water containing material.

Suitable crosslinkable polymers which may be used in the present invention include but are not limited to one or a mixture of polymers selected from the group consisting of polyhydroxy ethyl methacrylate, polyvinyl alcohol, polyacrylamide, poly (N-vinyl pyrolidone), polyethylene oxide, hydrolysed polyacrylonitrile, polyacrylic acid, polymethacrylic acid, polyethylene amine, alginic acid, pectinic acid, carboxy methyl cellulose, hyaluronic acid, heparin, heparin sulfate, chitosan, carboxymethyl chitosan, chitin, pullulan, gellan, xanthan, carboxymethyl starch, carboxymethyl dextran, chondroitin sulfate, cationic guar, cationic starch as well as salts and esters thereof. Polymers listed above which are not ionically crosslinkable are used in blends with polymers which are ionically crosslinkable.

The most preferred polymers include one or a mixture of alginic acid, pectinic acid, carboxymethyl cellulose, hyaluronic acid, chitosan, polyvinyl alcohol and salts and esters thereof. Preferred anionic polymers are alginic or pectinic acid; preferred cationic polymers include chitosan, cationic guar, cationic starch and polyethylene amine.

Other preferred polymers include esters of alginic, pectinic or hyaluronic acid and $C_2$ to $C_4$ polyalkylene glycols, e.g. propylene glycol, as well as blends containing 1 to 99 wt % of alginic, pectinic or hyaluronic acid with 99 to 1 wt % polyacrylic acid, polymethacrylic acid or polyvinylalcohol. Preferred blends comprise alginic acid and polyvinylalcohol.

The crosslinking ions used to crosslink the polymers may be anions or cations depending on whether the polymer is anionically or cationically crosslinkable. Appropriate crosslinking ions include but are not limited to cations selected from the group consisting of calcium, magnesium, barium, strontium, boron, beryllium, aluminum, iron, copper, cobalt, lead and silver ions. Anions may be selected from but are not limited to the group consisting of phosphate, citrate, borate, succinate, maleate, adipate and oxalate ions. More broadly, the anions are derived from polybasic organic or inorganic acids. Preferred crosslinking cations are calcium, iron, and barium ions. The most preferred crosslinking cations are calcium and barium ions. The most preferred crosslinking anion is phosphate. Crosslinking may be carried out by contacting the polymers with an aqueous solution containing dissolved ions.

As indicated above, the polymer hydrogels forming the shaped medical device of this invention are also crosslinked by non-ionic crosslinking mechanisms to produce a device having a higher crosslink density and one which has improved mechanical properties, i.e., improved stiffness, modulus, yield stress and strength. Th,is may be accomplished by additionally subjecting the ionically crosslinkable polymer to non-ionic crosslinking mechanisms such as high energy radiation (gamma rays) or treatment with a chemical crosslinking agent reactive with groups present in the polymer such that covalent bonds are formed connecting the polymer network. Another non-ionic crosslinking mechanism useful with respect to some classes of hydrogel polymers is physical crosslinking which is typically accomplished by crystal formation or similar association of polymer blocks such that the polymer molecules are physically tied together and prevented from complete dissolution. Non-ionic crosslinking may be carried cut prior to, subsequent to or concurrently with ionic crosslinking.

The most preferred method for non-ionic crosslinking is contact of the ionically crosslinkable polymer with a chemical crosslinking agent, because the degree of crosslinking can be more readily controlled, mainly as a function of the concentration of the crosslinking agent in the reaction medium. Suitable crosslinking agents are polyfunctional compounds preferably having at least two functional groups reactive with one or more functional groups present in the polymer. Preferably the crosslinking agent contains one or more of carboxyl, hydroxy, epoxy, halogen or amino functional groups which are capable of undergoing facile nucleophilic or condensation reactions at temperatures up to about 100° C. with groups present along the polymer backbone or in the polymer structure. Suitable crosslinking reagents include polycarboxylic acids or anhydrides; polyamines; epihalohydrins; diepoxides; dialdehydes; diols; carboxylic acid halides, ketenes and like compounds. A particularly preferred crosslinking agent is glutaraldehyde.

One of the unique properties of the polymer hydrogels of this invention is that the ionic crosslinks can be easily and selectively displaced in-vivo after implantation of the device in the body, resulting in a swelling and softening of the device in the body which enhances patient comfort. Since the non-ionic crosslinks are not significantly displaced, the device will retain its original non-ionically crosslinked shape configuration to a large degree and will not disintegrate.

For example, a biliary or urethral stent can be fabricated which has improved modulus (stiffness) properties due to the dual crosslinking treatment of this invention. Such a stent will be robust enough and be sufficiently resistant to buckling such that it can be readily inserted into the appropriate part of the body with an endoscope. Once inserted, the ionic crosslinks present in the device can be selectively at least partially stripped either directly by the physician, by dietary means or by means of natural body fluids such as bile or urine. As the ionic crosslinks are removed, the modulus of the device will be lowered and the device will soften and swell in body fluids, resulting in a more comfortable and conformable element and a larger lumen through which body fluids may flow. An enlarged lumen is typically preferred in tubular shaped devices to allow higher flow rates, to provide anchoring force to the body and to decrease the likelihood of occlusion during service.

Displacement of the crosslinking ions can be accomplished by flowing a solution containing a stripping agent around and/or through the :medical device in-vivo. The stripping agent serves to displace, sequester or bind the crosslinking ions present in the ionically crosslinked polymer, thereby removing the ionic crosslinks. The choice of any particular stripping agent will depend on whether the ion to be displaced is an anion or a cation. Suitable stripping agents include but are not limited to organic acids and their salts or esters, phosphoric acid and salts or esters thereof, sulfate salts and alkali metal or ammonium salts.

Examples of stripping agents include, but are not limited to, ethylene diamine tetraacetic acid, ethylene diamine tetraacetate, citric acid and its salts, organic phosphates such as cellulose phosphate, inorganic phosphates, as for example, pentasodium tripolyphosphate, mono and dibasic potassium phosphate, sodium pyrophosphate, phosphoric acid, trisodium carboxymethyloxysuccinate, nitrilotriacetic acid, maleic acid, oxalate, polracrylic acid, as well as sodium, potassium, lithium, calcium and magnesium ions. Preferred agents are citrate, inorganic phosphates and sodium, potassium and magnesium ions. The most preferred agents are inorganic phosphates and magnesium ions.

Specific methods for introduction of the stripping agent include introduction through the diet of the patient or through parenteral feeding, introduction of a solution directly onto the device such as by insertion of a catheter which injects the agent within the device, or through an enema.

For example, one dietary technique for stripping urinary device such as an implanted calcium alginate ureteral stent strippable by phosphate anions would be to include in the patient's diet materials which bind phosphate e.g., calcium salts, to lower the content of $PO_4^{-3}$ present in the urine which can be normally up to about 0.1%. When it is desired to strip the medical device, phosphate binders can be eliminated from the diet and also replaced by foods or substances which generate phosphate ions in the urine. Achievement of levels of phosphate in the urine of from 0.2 to 0.3% will result in the in-vivo stripping of the calcium ions from the calcium alginate stent. Lower levels of phosphate in the urine will also result in a more gradual stripping of the calcium ions, but higher levels are preferred for rapid stripping of the calcium.

Another advantage of the invention is that the stripping process may :be reversed to re-stiffen the medical device which facilitates surgical removal of the device from the body. This may be accomplished by flowing a source of crosslinking ions through and/or around the implant to ionically re-crosslink the implant, essentially the reverse of the stripping process described above. Dietary modifications can also be used to re-crosslink the medical device in-vivo.

In another embodiment of the invention, a secondary shape can be imparted to the medical device prior to implant in the body. This is accomplished by deforming the primary shape of a device which is crosslinked at least non-ionically, setting the device in the deformed shape by ionic crosslinking and implanting the device in the body in the deformed shape. Stripping the ions in-vivo as described above will cause the device to revert in-vivo to its primary non-ionically crosslinked shape. In accordance with one aspect of this embodiment, an ionically crosslinkable polymer is formed into a primary shape and subjected to non-ionic crosslinking conditions to form a non-ionically crosslinked hydrogel having said primary shape. Non-ionic crosslinking can be carried out by the methods described above, and is preferably carried out by extruding the polymer into a bath containing a sufficient amount of one or more of the non-ionic crosslinking agents to form a shape-retaining hydrogel. Next, a secondary shape is imparted to the non-ionically crosslinked hydrogel and the hydrogel is then subjected to ionic crosslinking conditions to ionically crosslink the hydrogel while retaining this secondary shape.

In another aspect of this embodiment, an ionically crosslinkable polymer is formed into a primary shape and subjected to both non-ionic and ionic crosslinking conditions to form a hydrogel having said primary shape and containing both an ionic and non-ionic crosslink structure. In accordance with this second aspect, an ionically and non-ionically crosslinked shaped hydrogel is prepared as above. Then, the shaped hydrogel is selectively stripped ex-vivo of at least a portion or essentially all of the crosslinking ions; the shaped hydrogel is conformed to a secondary shape, e.g., bent around a wire, stretched, compressed or the like; and the shaped hydrogel is ionically re-crosslinked while retained in the secondary shape. Release of the crosslinking ions in-vivo will cause the implanted device to revert substantially to the original primary, non-ionically crosslinked shape. The stripping step described above can occur immediately prior to or subsequent to the secondary shaping step, but preferably subsequent such step but prior to the ionic recrosslink step.

This embodiment is particularly useful where the medical device is of hollow, tubular configuration, such as a stent. Where the stent is both tonically and non-ionically crosslinked, it is selectively stripped of the crosslinking ions. The stent is stretched to form a narrower stent which facilitates insertion into the body, ionically crosslinked or re-crosslinked in the stretched state to fix the stent in the stretched state, implanted in the body and then re-stripped in-vivo of the ionic crosslinks to produce a softer implant having a wider lumen. Other stent shapes such as pigtail ends, flaps, curves and the like can be developed in-vivo by subjecting devices having these primary initial shapes to the process described above, i.e., deforming the primary shape ex-vivo and reforming the primary shape in-vivo.

The stripping step described above is preferably accomplished by dipping or spraying the crosslinked device with an aqueous electrolyte solution for an appropriate time to selectively strip the crosslinking ions from the device. Preferred electrolytes for ex-vivo stripping are chlorides of monovalent cations such as sodium, potassium or lithium chloride, as well as other stripping salts described above. The concentration of the electrolyte salt in the solution may range from about 1 wt % up to the solubility limit. The solution may also contain plasticizing ingredients such as glycerol or sorbitol to facilitate inter and intra polymer chain motion during and after secondary shaping.

Secondary shaping of the medical device may be done by hand, i.e., using pinning boards or jig pins, or by using shaped presses or molds.

The device may be ionically crosslinked or re-crosslinked in the secondary shape by contacting the device, while retaining the secondary shape, with an aqueous solution containing the crosslinking ions described above. After crosslinking, the device will essentially retain the secondary shape.

Medical devices which may be fabricated in accordance with this invention include stents, catheters or cannulas, plugs and constrictors, for both human and animal use. The invention is particularly applicable to medical stents of tubular configuration which come in contact with one or more body fluids such as blood, urine, gastrointestinal fluids and bile. The devices are particularly applicable for use in gastrointestinal, urogenital, cardiovascular, lymphatic, otorhinolaryngological, optical, neurological, integument and muscular body systems.

The devices may optionally include fillers, disintegration agents, additives for medical treatment such as antiseptics, antibiotics, anticoagulants, or medicines, and additives for mechanical property adjustment of the device.

Linear device or pre-device configurations such as fibers, rods, tubes or ribbons can be manufactured in accordance with the present invention by using a spinning device in which an aqueous solution of an ionically crosslinkable matrix polymer is forced through a shaping die into a crosslinking bath containing the crosslinking ions. The product after crosslinking is typically described as a hydrogel. The hydrogel may be used as made, or further given a three dimensional shape through treatment in a crosslinking solution after being forced into the desired shape. After equilibration, the hydrogel will retain the new three dimension shape. The device may be used in its hydrogel form or in a dehydrated form. During dehydration, the three dimensional shape is retained.

Another process for manufacturing the articles of the present invention comprises introducing a solution comprising ionically crosslinkable polymer through a die to form a tube, simultaneously pumping a solution comprising crosslinking ion through the formed tube, and extruding the formed tube from said die into a solution comprising crosslinking ion. In this process, the crosslinking step may involve shaping of the device as in wet spinning of a tubular device. Alternatively, the device may be prepared by molding a latent crosslinking composition using a one or two part reaction injection molding system. The term "tubular" as used herein, includes not only cylindrical shaped devices having circular cross sections, but also devices having different cross sections as long as such articles have a hollow passageway, which distinguishes a tube from a rod.

The ionically crosslinked, shaped polymer prepared as above is then subjected to non-ionic crosslinking, e.g. high energy radiation or by contact under appropriate acidic or basic conditions with the appropriate chemical crosslinking agent. Crosslinking is preferably carried out by soaking the polymer in an aqueous solution containing a water soluble crosslinking agent such as glutaraldehyde, ethylene diamine or a lower alkylene glycol. Generally, the concentration of crosslinking agent in solution may range from about 0.25 to about 10 wt %, more preferably from about 0.5 to 5.0 wt %. The degree of non-ionic crosslinking is controlled as a function of the concentration of the crosslinking agent in solution. The level should be selected such that a stiffer, higher modulus device is produced which will revert to a soft, stretchy, shape retaining device after removal of the ionic crosslinks. Some trial and error may be required to determine optimum levels depending on the particular polymer and the identity of the crosslinking agent.

The crosslinking process may also be conducted by first crosslinking the polymer non-ionically, followed by ionic crosslinking, essentially the reverse of the process described above.

Where the ionically crosslinkable polymer composition includes polymers which are partially water soluble, it is preferred to include in the aqueous spinning solution and treatment solutions described above one or more additives which retard the tendency of the solution to dissolve the polymer, i.e., provide non-solvent conditions. Example of such conditions include high salt concentrations, or inclusion in the solution of additives such as borax, boric acid, alkali metal salts and/or a lower alcohol such as methanol.

The various steps may be performed at any suitable temperature, e.g., at room temperature or at temperatures up to about 100° C. Preferably, soaking steps are conducted at room temperature. Moreover, the steps may be performed one immediately after another, or a drying step (e.g., air-drying) may be interposed between one or more steps. Additionally, the shaped medical device may be sterilized after the sequence of secondary-shaping steps.

The medical device may be stored wet or dry. For example, the medical device may be stored in a suitable aqueous solution or may be dried prior to storage. For example, the medical device could be stored in deionized water, or in water containing water soluble agents such as glycerol, sorbitol, sucrose and the like.

Exemplary hydrogel systems which may be prepared in accordance with this invention can be prepared by the following procedures:

a) Alginate which has been covalently and ionically crosslinked.

A solution of sodium alginate is extruded through a tube is into a calcium chloride bath while calcium chloride solution is simultaneously introduced through the lumen of the tube. This ionically crosslinked tube is then covalently crosslinked by treatment with an aqueous solution containing glutaraldehyde. The now covalently and ionically crosslinked gel has a higher crosslink density and therefore higher modulus than a similar tube having only the covalent or only the ionic crosslinks. The tube therefore has higher stiffness and improved resistance to buckling than a tube having the covalent or ionic crosslinks alone. After insertion into the body, exposure of the tube to ions in body fluids will remove the calcium crosslinks, lower the modulus of the gel and therefore reduce the stiffness of the tube, allowing for maximum patient comfort and biocompatibility. Suitable ions which will displace the calcium crosslinking ions include phosphate, sulfate, carbonate, potassium, sodium and ammonium. The implanted device may be stiffened and strengthened during removal from the body via exposure of the device to an infusion fluid which contains a solution of the crosslinking ions (calcium).

b) Polyvinyl alcohol and alginate.

A blend of polyvinyl alcohol (PVA) and sodium alginate may be dispersed or dissolved in water, extruded into a bath containing calcium ions, said bath also containing non-solvent conditions for the polyvinyl alcohol. The polyvinyl alcohol component of the formed article may then be covalently crosslinked with an aqueous solution containing glutaraldehyde. The article is now ready for insertion or implantation. After implantation, the article may be softened and swollen by removal of the ionic crosslinks as above. Removal of the ionic crosslinks may also optionally allow the alginate to fully or partially dissolve in the body fluids, leaving behind a less dense, more porous hydrogel. The morphology of the final hydrogel device may be controlled through judicious selection of polyvinyl alcohol molecular weight, degree of crosslinking, solvent composition, alginate molecular weight, alginate salt used, state of the alginate salt (dissolved, particulated, gel), alginate monomer makeup, temperature, pressure, mix time, solution age, and rheological factors during manufacture.

c) Polyvinyl alcohol and alginate shape memory. The blend of PVA and sodium alginate described in (b) above may be used to make a stent having a shape memory feature to gain increased lumen size after deployment in-vivo. A tube is made by extruding the mixture through a tube die into a concentrated calcium chloride bath, optionally containing other salts and boric acid. The tube is then transferred into a bath which contains calcium chloride and a chemical crosslinker (glutaraldehyde). After allowing for reaction, the tube will become a covalently crosslinked PVA/calcium alginate system. The tube is immersed in concentrated potassium chloride solution to remove the calcium crosslinks from the alginate while preventing the alginate from dissolving. The tube is then stretched to form a longer length tube having a more narrow lumen. While in this stretched configuration, the tube is immersed into concentrated calcium chloride solution to re-crosslink the alginate. The tube is frozen into the longer length, narrow lumen configuration. Upon insertion into the body, the tube will return to it's original shorter length, large lumen configuration as the calcium is stripped from the alginate. The alginate may eventually dissolve, leaving behind a more porous glutaraldehyde crosslinked PVA tube. Other imposed shapes may be used to accommodate body insertion in a compact form, followed by shape change upon displacement of the ionic crosslinks.

d) Propyleneglycol alginate.

Propyleneglycol alginate may be covalently crosslinked with ethylene diamine under basic conditions and ionically crosslinked with calcium ions. This covalently and ionically crosslinked material will exhibit higher stiffness than the material crosslinked with covalent linkages only. Removal of the ionic crosslinks will occur in-vivo after deployment in body fluid. A stent, catheter or cannula can be manufactured from this material, implanted while both ionically and covalently crosslinked, then in-vivo the device will soften as the ionic crosslinks are displaced. A device of this construction would provide stiffness for implantation and softness for patient comfort.

EXAMPLE 1

This example illustrates the preparation of tubing from a mixture of sodium alginate (Protanol LF 10/60 from Pronova Bipolymers A.S., Drammen, Norway) and polyvinylalcohol (PVA). A series of four different formulations were prepared as shown in Table 1.

TABLE 1

| PVA/alginate (wt. rat.) | 15/5 | 20/5 | 15/7.5 | 20/5 |
|---|---|---|---|---|
| Deionized water | 72 g | 67.5 g | 69.7 g | 74.25 g |
| PVA | 13.5 g | 18.0 g | 13.5 g | 19.8 g |
| Sodium alginate | 4.5 g | 4.5 g | 6.75 g | 4.95 g |
| Bismuth subcarbonate | 9.68 g | 9.77 g | 9.69 g | 9.9 g |

The deionized water was weighed into a 4 oz. jar, while stirring the water, the PVA and sodium alginate were added and mixed until uniform. The jar was capped and heated to 100° C. to dissolve the ingredients. The jar was cooled to 37° C., then the bismuth subcarbonate (radiopaque filler) which had been sifted through a 325 mesh screen was added and the composition was mixed with a jiffy mixer until uniform. The samples were loaded into 30 cc syringes, centrifuged to remove air, then extruded through a tubing die into a coagulant solution. The coagulant solution was made from 100 grams of calcium chloride dihydrate, 30 grams of sodium chloride, 50 grams of boric acid and 820 grams of deionized water. The spun tubing was left in the coagulant solution overnight. Lengths of tubing were then soaked in a glutaraldehydle/coagulant solution mixture to covalently crosslink the sample. Glutaraldehyde levels were tested from 0.5% by weight to 12.5% by weight. pH was adjusted to 1.5 using 20% HCL solution. After reacting overnight at room temperature, the tubes were examined and then immersed in 0.4% sodium phosphate solution to strip the ionic crosslinks. Results are recorded in Table 2.

TABLE 2

| Glutaraldehyde (wt %) | 0.5% | 1.0% | 5.0% | 12.5% |
|---|---|---|---|---|
| 15/5 (PVA/Alginate wt. ratio) | soft, stretchy | slightly stiffer | stiffer, but still soft | stiff, brittle |
| 15/7.5 (PVA/Alginate wt. ratio) | soft, stretchy | slightly stiffer | much stiffer | stiff, brittle |
| 20/5 (PVA/Alginate wt. ratio) | soft, stretchy | slightly stiffer | stiff, brittle | stiff, brittle |

Control samples which were not treated with glutaraldehyde were swollen and broken apart in the phosphate solution.

What is claimed is:

1. A method for forming a shaped medical device, comprising the steps of:
   (a) providing a crosslinkable polymer, crosslinking the crosslinkable polymer with at least one non-ionic crosslink, and shaping the crosslinked polymer to form a device having a primary shape; and
   (b) deforming the device comprising the primary shape by providing ions and ionically crosslinking the device comprising the primary shape, producing a device having a secondary shape.

2. The method of claim 1, wherein the device having the secondary shape is implanted in the body of a mammal.

3. The method of claim 1 or 2, further comprising after step (b), the step (c) of removing the ions, thereby restoring the device having the secondary shape to its primary shape.

4. A method for forming a shaped medical device, comprising the steps of:
   (a) providing a crosslinkable polymer;
   (b) crosslinking the crosslinkable polymer to produce a crosslinked polymer having both ionic and non-ionic crosslinks;
   (c) shaping the crosslinked polymer to form a device having a primary shape; and
   (d) deforming the primary shape by selectively removing the ionic crosslinks to form a device having a secondary shape.

5. The method of claim 4, further comprising after step (d), the step of re-ionically crosslinking the device having the secondary shape.

6. The method of claim 4, wherein the device having the secondary shape is implanted in the body of a mammal.

7. The method of claim 6, further comprising the step of removing the crosslinking ions, thereby causing the device to revert to its primary shape.

8. The method of claim 4, wherein both the device having the primary shape and the device having the secondary shape comprise a hollow tube and wherein the lumen of the device having the primary shape is larger than the lumen of the device having the secondary shape.

9. A method of changing the shape of a shaped medical device in vivo in the body of a mammal, comprising the steps of:
   (a) providing a shaped medical device having at least non-ionic crosslinks; and
   (b) providing in vivo a source of ions in and around the device and ionically crosslinking the device.

10. The method of claim 9, wherein the shaped medical device comprises both ionic and non-ionic crosslinks.

11. The method of claim 9, further comprising the step (c) of removing the shaped medical device from the body of the mammal.

12. The method of claim 11, wherein step (b) is performed prior to step (c).

13. The method of claim 1, 4, or 9, wherein the crosslinkable polymer comprises a cationic polymer aid the ions are anions selected from the group consisting of phosphate, citrate, borate, succinate, maleate, adipate, and oxalate ions.

14. The method of claim 1 or 4, wherein the primary shape is the shape of a stent, catheter, plug, constrictor, or biological encapsulant.

15. The method of claim 9, wherein the shaped medical device has the shape of a stent, catheter, plug, constrictor, or biological encapsulant.

16. The method of claim 1, 4, or 9, wherein the non-ionic crosslinks are covalent crosslinks.

17. The method of claim 1, 4, or 9, wherein the crosslinkable polymer comprises one or a mixture of polymers, selected from the group consisting of polyhydroxyethylmethacrylate, polyvinyl alcohol, polyacrylamide, poly (N-vinyl pyrolidone), polyethylene oxide, hydrolyzed polyacrylonitrile, polyacrylic acid, polymethacrylic acid, polyethylene amine, alginic acid, pectinic acid, carboxy methyl cellulose, hyalurcnic acid, heparin, heparin sulfate, chitosan, carboxymethyl chitosan, chitin, pullalan, gellan, xanthan, carboxymethyl starch, carboxymethyl dextran, chondroitin sulfate, cationic guar, cationic starch, and salts and esters thereof.

18. The method of claim 1, 4, or 9, wherein the crosslinkable polymer comprises one or a mixture of cationic polymers selected from the group consisting of chitosan, cationic guar, cationic starch, and polyethylene amine.

19. The method of claim 1, 4, or 9, wherein the crosslinking is performed by providing a crosslinking agent selected from the group consisting of carboxyl, hydroxy, epoxy, halogen, and amino functional groups.

20. The method of claim 1, 4, or 9, wherein the non-ionic crosslinks are formed by providing a crosslinking agent is selected from the group consisting of glutaraldehyde, epichlorohydrin, dianhydrides, and diamines.

21. The method of claim 20, wherein the crosslinking agent is glutaraldehyde.

22. The method of claim 17, wherein the crosslinkable polymer comprises alginic acid.

23. The method of claim 22, wherein said crosslinkable polymer comprises an ester of alginic acid and a $C_2$ to $C_4$ alkylene glycol.

24. The method of claim 23, wherein the alkylene glycol is propylene glycol.

25. The method of claim 17, wherein the crosslinkable polymer comprises a mixture of alginic or pectinic acid, and polyvinyl alcohol.

26. The method of claim 1, 4, or 9, wherein the shaped medical device is in the form of a cylindrical, hollow tube.

27. The method of claim 3 or 4, wherein the step of selective removing occurs prior to the step of forming non-ionic crosslinks.

28. The method of claim 3 or 4, wherein the step of selective removing occurs in the body.

29. The method of claim 3 or 4, wherein the step of selective removing is done by using a stripping agent.

30. The method of claim 29, wherein the stripping agent is selected from the group consisting of ethylenediaminetetracetic acid, ethylenediaminetetraacetate, organic phosphates, inorganic phosphates, sodium ions, potassium ions, lithium ions, calcium ions, and magnesium ions.

* * * * *